United States Patent
Smith et al.

(10) Patent No.: US 8,825,568 B2
(45) Date of Patent: Sep. 2, 2014

(54) HEALTH CARE INCIDENT PREDICTION

(75) Inventors: Mike Smith, Toronto (CA); Sanjay Malaviya, Mississauga (CA)

(73) Assignee: Radicalogic Technologies, Inc., Toronto, Ontario (CA)

( * ) Notice: Subject to any disclaimer, the term of this patent is extended or adjusted under 35 U.S.C. 154(b) by 77 days.

(21) Appl. No.: 13/489,928

(22) Filed: Jun. 6, 2012

(65) Prior Publication Data

US 2013/0144816 A1    Jun. 6, 2013

Related U.S. Application Data

(60) Provisional application No. 61/493,799, filed on Jun. 6, 2011.

(51) Int. Cl.
- *G06N 5/00*    (2006.01)
- *G06F 1/00*    (2006.01)
- *G06N 99/00*   (2010.01)

(52) U.S. Cl.
CPC .................................. *G06N 99/005* (2013.01)
USPC ................................ 706/12; 600/544; 702/19

(58) Field of Classification Search
USPC ............................................................ 706/12
See application file for complete search history.

(56) References Cited

U.S. PATENT DOCUMENTS

| | | | |
|---|---|---|---|
| 2007/0055552 A1* | 3/2007 | St. Clair et al. | 705/3 |
| 2009/0227877 A1* | 9/2009 | Tran | 600/483 |
| 2010/0042329 A1* | 2/2010 | Hood et al. | 702/19 |

* cited by examiner

*Primary Examiner* — Alan Chen
*Assistant Examiner* — Kalpana Bharadwaj
(74) *Attorney, Agent, or Firm* — Norton Rose Fulbright Canada LLP (57) ABSTRACT

Embodiments described herein relate to apparatuses and methods for incident prediction alerts for transmission to a health care organization system by applying rules to data sets. Each rule may define a set of data elements linked to an incident, and a processor may detect one or more sets of data elements in the data sets. The processor may normalize the data feeds, generate rules on historical data, generate prediction alerts by applying rules to near-real time data feeds, train to update rules, validate and error check rules, remove statistical noise, generate visualizations for the data feeds, and receive input and feedback data.

21 Claims, 3 Drawing Sheets

FIG. 3

HEALTH CARE INCIDENT PREDICTION

FIELD

The described embodiments relate to systems and methods for predicting incidents and, in particular, to systems and methods for predicting health care incidents.

INTRODUCTION

A healthcare organization creates and collects large amounts of data, such as billing data, patient admission data, human resources data, incident data and so on.

There exists a need for improved systems and methods for analyzing and using the data created and collected by healthcare organizations, or at least alternatives.

BRIEF DESCRIPTION OF THE DRAWINGS

For a better understanding of embodiments of the systems and methods described herein, and to show more clearly how they may be carried into effect, reference will be made, by way of example, to the accompanying drawings in which.

The drawings, described below, are provided for purposes of illustration, and not of limitation, of the aspects and features of various examples of embodiments described herein. The drawings are not intended to limit the scope of the applicants' teachings in any way. For simplicity and clarity of illustration, elements shown in the figures have not necessarily been drawn to scale. The dimensions of some of the elements may be exaggerated relative to other elements for clarity. Further, where considered appropriate, reference numerals may be repeated among the figures to indicate corresponding or analogous elements.

DESCRIPTION OF EXEMPLARY EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing implementation of the various embodiments described herein.

In a first aspect embodiments, described herein may provide an apparatus comprising a processor and a memory storing instructions which when executed configure the processor to generate incident prediction alerts for transmission to a health care organization system by applying rules to data sets. Each rule may define a set of data elements linked to an incident, and the processor may be further configured to detect one or more sets of data elements in the data sets. Rules may also be described herein as patterns and pattern matching algorithms, and may be developed by correlating data common to incident occurrences, guides, and user input data and feedback.

In accordance with some embodiments, the data sets may comprise historical data sets relating to incidents that have occurred in the health care organization, and the processor may be further configured to develop rules by, for each incident, training on the historical data sets to identify a set of data elements that is common to one or more occurrence of the incident in the health care organization.

In accordance with some embodiments, wherein each rule may be linked to a healthcare incident. In accordance with some embodiments, each data element may correspond to a type and a value.

In accordance with some embodiments, the data sets may comprise near-real time data feeds regarding machines, devices and patients of the health care organization and other data relevant to the health care organization for incident prediction.

In accordance with some embodiments, the processor may be further configured to train on the historical data sets to determine the probability of incident occurrence, and wherein incident prediction alerts are generated using the probability of incident occurrence.

In accordance with some embodiments, the processor may be further configured to provide a visualization of one or more data feeds to receive input data has a guide for training the processor to develop rules.

In accordance with some embodiments, an incident may be linked to a plurality of rules for generating prediction alerts relating thereto.

In accordance with some embodiments, the processor may be configured to provide an interface for reporting incident occurrences and receiving data feeds relating to the incident occurrences.

In accordance with some embodiments, the processor may be configured to periodically train on updated data feeds to update the rules.

In accordance with some embodiments, the processor may be configured to assign weights to at least one data element of a set of data elements of a rule.

In accordance with some embodiments, the processor may be configured to query for user input data in response to the incident alerts to further train and update the rules.

In accordance with some embodiments, the processor may be configured to provide incident prevention messages as part of the incident alerts.

In accordance with some embodiments, the processor may be configured to monitor user response to the incident alerts to train and update the rules.

In accordance with some embodiments, the processor may be configured to integrate data feeds from data collected by health care organization and third party organizations.

In accordance with some embodiments, the processor may be configured to normalize the data feeds, generate rules on historical data, generate prediction alerts by applying rules to near-real time data feeds, train to update rules, validate and error check rules, remove statistical noise, generate visualizations for the data feeds, and receive input and feedback data.

In another aspect, embodiments described herein may provide a system for health care incident alerts comprising an apparatus comprising a processor and a memory storing instructions which when executed configure the processor to generate incident prediction alerts for transmission to a health care organization system by applying rules to data sets. Each rule may define a set of data elements linked to an incident, and the processor may be further configured to detect one or more sets of data elements in the data sets, where the apparatus is connected via a network to a plurality of clients accessed by user stations of the health care organization, and a data repository. The apparatus is configured to receive input data from the clients and provide output data to the clients. The apparatus is further configured to store incident data in the data repository. The apparatus may be configured to connect via the network to devices within the health care organization to receive data feeds therefrom. The apparatus may be configured to connect via the network to machines within the health care organization to receive data feeds therefrom.

In a further aspect, embodiments described herein may provide non-transitory computer readable medium with instructions encoded thereon to configure a processor to generate incident prediction alerts for transmission to a health care organization system by applying rules to data sets, wherein each rule defines a set of data elements linked to an incident, and to further configure the processor to detect one or more sets of data elements of the rules in the data sets. The data sets may comprise historical data sets relating to incidents that have occurred in the health care organization, and the instructions may further configure the processor to develop rules by, for each incident, training on the historical data sets to identify a set of data elements that is common to one or more occurrence of the incident in the health care organization. The data sets may comprise near-real time data feeds regarding machines, devices and patients of the health care organization and other data relevant to the health care organization for incident prediction, and the instructions may further configure the processor to monitor the near-real time data feeds and apply rules thereto in order to generate timely incident prediction alerts.

The embodiments of the systems and methods described herein may be implemented in hardware or software, or a combination of both. However, these embodiments may be implemented in computer programs executing on programmable computers, each computer including at least one processor, a data storage system (including volatile and non-volatile memory and/or storage elements), and at least one communication interface. For example, the programmable computers may be a server, network appliance, set-top box, embedded device, computer expansion module, personal computer, laptop, personal data assistant, or mobile device. Program code is applied to input data to perform the functions described herein and to generate output information. The output information is applied to one or more output devices, in known fashion. In some embodiments, the communication interface may be a network communication interface. In embodiments in which elements of the invention are combined, the communication interface may be a software communication interface, such as those for inter-process communication. In still other embodiments, there may be a combination of communication interfaces.

Each program may be implemented in a high level procedural or object oriented programming or scripting language, or both, to communicate with a computer system. However, alternatively the programs may be implemented in assembly or machine language, if desired. In any case, the language may be a compiled or interpreted language. Each such computer program may be stored on a storage media or a device (e.g. ROM or magnetic diskette), readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product including a physical non-transitory computer readable medium that bears computer usable instructions for one or more processors. The medium may be provided in various forms, including one or more diskettes, compact disks, tapes, chips, magnetic and electronic storage media, and the like. The computer useable instructions may also be in various forms, including compiled and non-compiled code.

Figure 1:
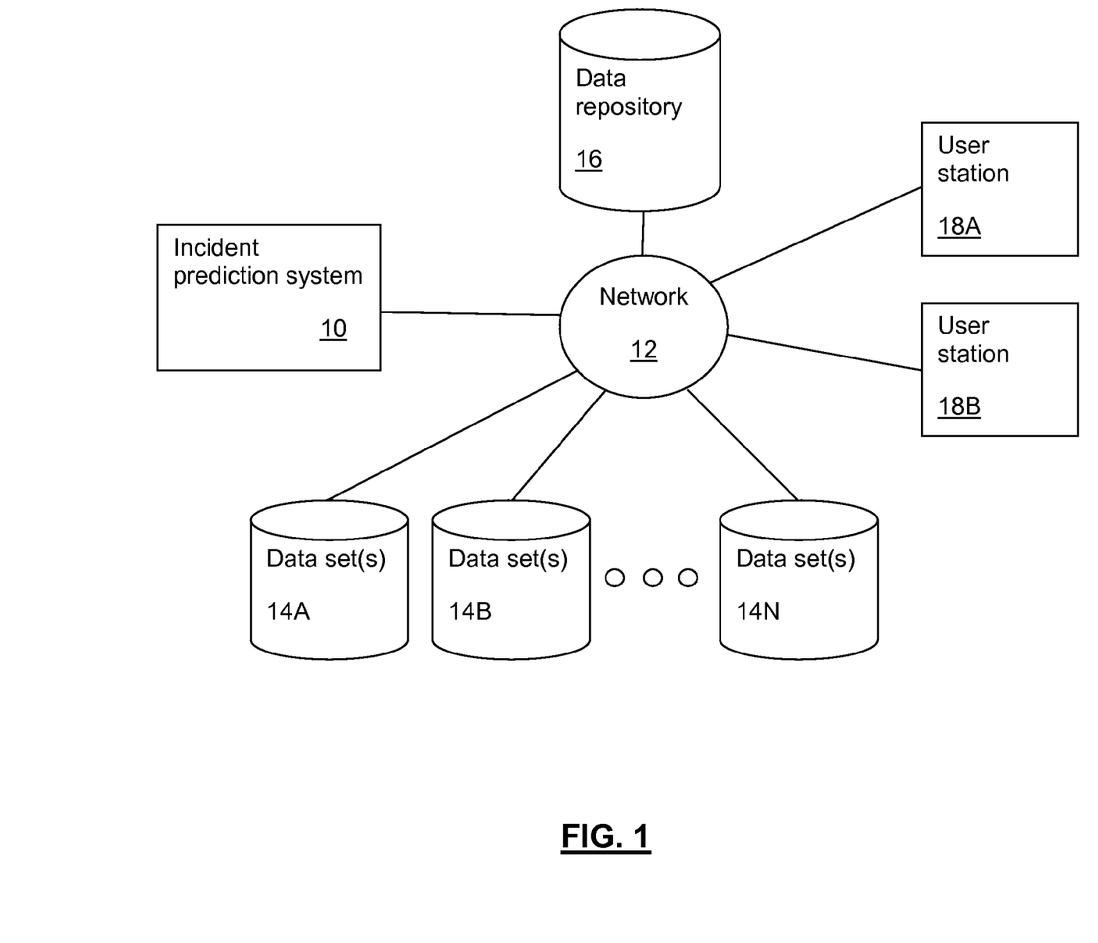
FIG. 1 is a block diagram of a system for predicting health care incidents in accordance with at least one embodiment.

Reference is first made to FIG. 1, which illustrates a block diagram of a system 10 for predicting a health care incident in accordance with at least one embodiment. As shown, an incident prediction system 10 connects to data set(s) 14A, 14B, . . . 14N related to one or more healthcare organizations, a data repository 16, and user stations 18A, 18B via a network 12.

Incident prediction system 10 is operable to analyze and process the data created or collected by one or more healthcare organizations. Incident prediction system 10 is further operable to provide an interface of various visualizations of different subsets of data created or collected by one or more healthcare organizations. The incident prediction system 10 is operable to generate healthcare prediction alerts by applying pattern matching algorithms or rules to input data received as data sets 14A, 14B, . . . 14N to detect the presence of one or more sets of key variables in the data sets 14A, 14B, . . . 14N related to a healthcare organizations. An incident prediction may be predict, indicate or otherwise determine that a healthcare incident has occurred or will likely occur. The data sets 14A, 14B, . . . 14N includes the data created or collected by the healthcare organization, as well as other data that may potentially relate to healthcare incidents. The incident prediction system 10 is operable to provide output results in the form of health care incident prediction alerts and visualizations so that an end user can make a decision relating to the health care incident in (near) real-time and proactively respond to issues which may prevent the occurrence of health care incidents.

Incident prediction system 10 is operable to convert or transform raw input data from data sets 14A, 14B, . . . 14N into incident related information that might assist healthcare organizations staff in incident decision-making. Incident management system 10 may be implemented as a physical server that resides within a healthcare organization's information technology system or may be an external server connected thereto via network 12.

Incident management system 10 receives input data related to a healthcare organization through data sets 14A, 14B, . . . 14N collected, created, or otherwise related to the healthcare organization (or in some cases multiple healthcare organizations) or incidents. A data set 14A, 14B, . . . 14N may be data in various forms such as raw input data, pre-processed input data, a specific format of input data, a data feed, a data stream, a data file, and so on. Each data set 14A, 14B, . . . 14N related to a healthcare organization may be composed of one data set or multiple data sets. The data sets 14A, 14B, . . . 14N may be received from a variety of sources such as internal databases located within the healthcare organization or external third party data databases. The data sets 14A, 14B, . . . 14N may be historical data sets, recent data sets or (near) real-time data sets. Example data sets 14A, 14B, . . . 14N include inventory records, consumption records, usage records, government records, device records, product recall records, error records, police records, security records, maintenance records, financial records, scheduling records, lab records, radiology records, surgery records, pharmacy records, EMR records, staffing records, shift records, billing records, administration records, admission records, patient records, hazardous material records, surveillance records, order records, calendar records, temperature records (both inside the healthcare organization and outside), network records, information technology records, and so on. By receiving input data from multiple data sets 14A, 14B, . . . 14N, incident prediction system 10 is operable to transform all data related to a healthcare organization and incidents, no matter the system or format the data resides in, into meaningful data that can be used by the healthcare organization for a variety of different purposes relating to incident management. Incident prediction system 10 is operable to analyze the data relating to a healthcare organization for use in new ways relating to incidents and receive feedback data relating to the incident alerts to further refine and develop pattern matching algorithms.

In accordance with some embodiments, the data set(s) 14A, 14B, . . . 14N may be specific to a given healthcare organization and processed by incident prediction system 10 to predict health care incidents. An incident is an event related to the healthcare organization that may have been reported to a healthcare organization. An incident may be an adverse event that occurred or almost occurred (i.e. a near miss) involving a patient of the health care organization. An incident may involve unsafe condition. Examples of incidents include but are not limited to medication incidents, patient incidents, protocol violations, procedural incidents, equipment failure, medical supply failure, loss of equipment, technical communication failure, and so on. Incident prediction system 10 may form part of or integrate with an existing healthcare incident management system that is operable to receive, process and store data relating to health care incidents, such as incident file summaries, patient records, maintenance records, and so on.

Incident prediction system 10 may receive historical data about incidents that have occurred or almost occurred from incident records and one or more data sets 14A, 14B, . . . 14N that relate to incidents. Incident prediction system 10 may integrate with an incident reporting system to receive incident records, or may provide an internal incident reporting system to receive incident data. Incident records may include data collected from staff of the health care organization defining a particular incident, including but not limited to a particular incident type, location, patient, date, time, and other information relating to the incident. For example, a healthcare incident reporting system may be operable to generate an electronic form for receiving data pertaining to healthcare incidents, where the form includes form fields that are operable to receive values pertaining to the healthcare incidents, such as the patient information, healthcare provider information, a description of the incident, names of other people involved in the incident, medication involved in the incident, a device involved in the incident, the date of the incident the location of the incident in the time of the incident, for example. The healthcare incident reporting system is operable to provide the incident related data (incident records) to the incident prediction system 10 as part of one or more data sets 14A, 14B, . . . 14N. A healthcare incident may be any event of interest to the healthcare organization, and generally is an adverse event that has occurred or almost occurred. For example, patient A may be diabetic and may require three insulin injections daily. A nurse may mistakenly give patient B an insulin injection instead of patient A. upon discovering the error, the nurse may input the incident into the healthcare incident management system to indicate that patient B received an unnecessary insulin injection and that patient A missed a required insulin injection. This data will be provided to incident prediction system 10 as part of an incident record in one or more data sets 14A, 14B, . . . 14N.

Incident prediction system 10 may be used for (near) real-time incident or error alerting and prevention. By receiving data sets 14A, 14B, . . . 14N from multiple systems related to the healthcare organization, incident prediction system 10 may determine, for example, if the wrong medication has been issued or is likely to be issued to a patient and could alert a healthcare staff in near real-time which may prevent or alleviate an incident. Incident prediction system 10 is operable to analyze near real time data sets 14A, 14B, . . . 14N irrespective of the fact that the input data is received from multiple systems related to the healthcare organization that may be separate, independent, not interoperable, not connected, or not compatible. In addition, incident prediction system 10 is operable to monitor input data and data sets 14A, 14B, . . . 14N in order to analyze the input data to detect patterns in the input data and automatically generate pattern matching algorithms or rules linked to incidents. Incident prediction system 10 can use the pattern matching algorithms to predict the occurrence of an incident and can generate an incident alert which may prevent or alleviate the incident. That is, incident prediction system 10 can automatically generate pattern matching algorithms and apply those algorithms to monitor near real-time data sets 14A, 14B, . . . 14N in order to automatically generate alerts relating to incident predictions. For example, incident prediction system 10 may identify key variables that are simultaneously present each time a given incident occurs and generate a rule or pattern containing those key variables. Incident prediction system 10 may then monitor near real-time input data from data sets 14A, 14B, . . . 14N and apply the generated rules or patterns to such near real-time input data. Upon detecting set of data points that meet the rule or pattern, incident prediction system 10 may generate an alert for incident prediction the next time those key variables are identified in monitored input data.

As another example, incident prediction system 10 may monitor input data for comparison or benchmarking purposes to generate alerts for events (incidents) that relate to the healthcare organization. For example, incident prediction system 10 may monitor billing data to determine how much money is coming into the healthcare organization and leaving the health care organization on a daily basis and generate an alert if a threshold amount is exceeded. Further, incident prediction system 10 may compare that data to other similar healthcare organizations (or between departments or facilities of the same healthcare organization) to provide a benchmarking or comparison tool. Further, incident prediction system 10 may share a subset of rules or patterns between healthcare organizations. As a further example, incident prediction system 10 can analyze surveillance and security related data to generate alerts relating to crime related incident predictions.

Incident prediction system 10 is operable to integrate with the health care organization's existing information technology systems for interoperability with data sets 14 and user stations 18.

Data repository 16 is operable to store some or all of the data sets 14A, 14B, . . . 14N used by incident prediction system 10 so that data repository 16 can potentially store all the data related to a particular healthcare organization, or multiple healthcare organizations. Although shown as a separate component connected via network 12, data repository 16 may be internal to incident prediction system 10. Data repository 16 may contain historical data and may also be continuously updated in near real time with new data so that incident prediction system 10 can monitor data related to the health care organization in near real time to generate alerts for incidents.

Network 12 may be any network(s) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these. Although not shown, incident prediction system 10, data sets 14A, 14B, ... 14N, data repository 16, user station 18A, 18B, and other components (not shown) may connect to network 20 via a firewall, which is a device, set of devices or software that inspects network traffic passing through it, and denies or permits passage based on a set of rules and other criteria. Firewall may be adapted to permit, deny, encrypt, decrypt, or proxy all computer traffic between network 12, incident prediction system 10, data sets 14A, 14B, ... 14N, data repository 16, user station 18A, 18B, and other components based upon a set of rules and other criteria. For example, firewall may be a network layer firewall, an application layer firewall, a proxy server, or a firewall with network address translation functionality. Network 12 is operable to secure data transmissions using encryption and decryption.

User station 18A, 18B is operable by a user, such as a healthcare organization staff or administrator, and may be any networked computing device including a processor and memory, such as a personal computer, workstation, server, portable computer, mobile device, personal digital assistant, laptop, smart phone, WAP phone, an interactive television, video display terminals, gaming consoles, an electronic reading device, and portable electronic devices or a combination of these. Although only two user stations 18A, 18B are illustrated in FIG. 1, there may be more user stations 18A, 18B connected via network 12. User stations 18A, 18B may include a client which may be a computing application, application plug-in, a widget, instant messaging application, mobile device application, e-mail application, online telephony application, java application, web page, or web object residing or rendered on the user stations 18A, 18B in order to access the functionality of incident prediction system 10. User station 18A, 18B is operable by a user to, for example, configure pattern matching algorithms, provide input data (including incident data), receive incident prediction alerts, configure incident prediction system 10, display visualizations of incident data, access data repository 16, and data sets 14A, 14B, ... 14N, provide feedback based on a received alert, assign weights to variables, and other functionality. User station 18A, 18B is operable to register users and authenticate users (using a login and password for example) prior to providing access to incident prediction system 10. User stations may be different types of devices and may serve one user or multiple users.

Figure 2:
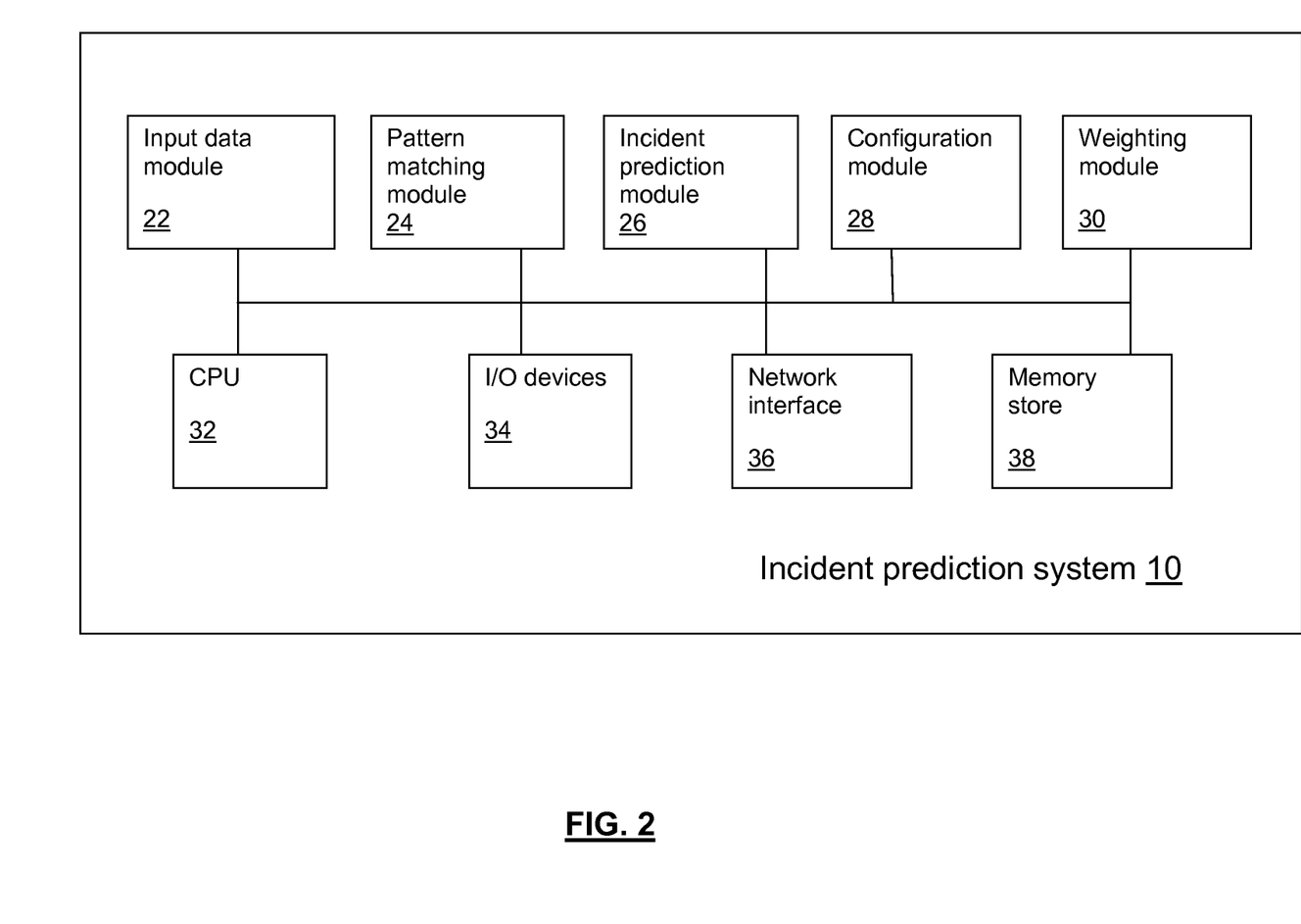
FIG. 2 is a block diagram of a system for predicting health care incidents in further detail and in accordance with at least one embodiment.

Referring now to FIG. 2, there is shown an incident prediction system 10 in further detail. Incident prediction system 10 may comprises one or more servers with computing processing abilities and memory such as database(s) or file system(s). For example, incident prediction system 10 may include a mail server, web server, database server, application server, and so on. Although only one incident prediction system 10 is shown for clarity, there may be multiple incident prediction system 10 or groups of incident prediction system 10 distributed over a wide geographic area and connected via e.g. network 12. A single incident prediction system 10 may serve a single health care organization or multiple healthcare organizations. In addition, multiple incident prediction systems 10 may serve a single health care organization in an integrated fashion, if for example a single health care organization is spread across different geographic locations. Incident prediction system 10 is operable to generate a healthcare organization profile for each healthcare organization managed by incident prediction system 10 to associate data sets 14A, 14B, ... 14N related to a specific healthcare organization. The healthcare organization profile may include a health care organization identifier.

The incident prediction system 10 analyzes the raw data sets 14A, 14B, ... 14N, by aggregating data relevant to a healthcare organization, normalizing the data sets into a standardized data format, generating pattern matching algorithms or rules to predict incidences, receiving feedback from users to refine patterns and rules, validating or error checking, identifying key variables that relate to specific incidents, identifying incidents that are likely to occur, removing bias or statistical noise in the data (examples of validation), and processing of the data so that it can be more easily or completely understood including but not limited to correlating input data based on an incident, patient, location, date, time or other environmental and contextual data, and summarizing results and data in charts, graphs, tables and any other form of visualization for presentation, and other forms of analysis.

In an exemplary embodiment, incident prediction system 10 has associated with it an input data module 22, a pattern matching module 24, an incident prediction module 26, a configuration module 28, a weighting module 30, a CPU 32, input and output devices 34, a network interface 36 and memory store 38.

Input data module 22 is operable to receive and monitor input data for data sets 14A, 14B, ... 14N and data repository 16. Input data module 22 is operable filter the input data and to correlate received input data based on an incident, date, time, and location of the healthcare organization or unit or department thereof in order to generate patterns or rules. Input data module 22 correlates the received input data based on incident, date, time, or location to identify relationships between separate data sets 14A, 14B, ... 14N with common data elements, to filter the input data and to facilitate benchmarking or comparisons amongst the received input data.

Input data module 22 is operable to normalize the input data from data set(s) 14A, 14B, ... 14N into a standardized format. Normalizing input data into a standardized format may assist when comparing and correlating data sets 14A, 14B, ... 14N. For example, a healthcare organization may include information technology systems that communicate using a universal language protocol such as HL7 messages. Input data module 22 is operable to receive these messages and translate them into a standard data format to merge these types of data sets with other types of data sets that are not originally in a standardized format. Input data module 22 may receive input data from other systems that use a different format, such as a human resource system, accounting system, inventory system, information technology system and so on, and translate this input data into the same standard data format. That is input data module 22 is operable to preprocess or normalize all received input data from a wide variety of formats to translate it into the standard data format.

The input data module 22 is also operable to tag the received input data with metatags that describe the input data to provide context to the input data for use by incident prediction system 10. Incident prediction system 10 is operable to provide visualizations of data from data sets 14A, 14B, ... 14N to user to configure metatags for the data to provide context for the data.

Pattern matching module 24 is operable to generate and manage pattern matching algorithms linked to incidents. A pattern matching algorithm or rule defines key variables linked to a specific incident. When the combination of key variables defined by a rule or pattern are present in near real time data from data sets 14A, 14B, ... 14N then this suggests a sufficient likelihood that an incident is about to occur and that an alert should be generated. A pattern matching algorithm may also define an incident that is linked to another incident, such that when one incident occurs, along with a particular set of data then this may suggest a sufficient likelihood that another incident may occur and that an alert should be generated. A pattern matching algorithm may define a narrow or wide set of variables.

Pattern matching module 24 is operable to develop pattern matching algorithms that will be applied to monitor near real-time input data from data sets 14A, 14B, ... 14N in order to detect or flag that a specific incident is likely to occur if a set of variables defined by a pattern or rule is present in the monitored input data. Pattern matching module 24 is operable to automatically develop pattern matching algorithms linked to specific incidents, to be manually configured with pattern matching algorithms, or a combination thereof. Further, pattern matching module 24 is operable to output or receive defined patterns to or from other incident prediction systems 10 for other health care organizations, so that health care organizations can share patterns and rules for general incidents that may not be specific to their organization.

Pattern matching module 24 is operable to implement heuristic and learning techniques on input data from data sets 14A, 14B, ... 14N and data stored in the data repository 16 to automatically develop pattern matching algorithms linked to incidents. Pattern matching module 24 may calibrate or learn for an initial time period, such as a few months for example, to gather reported incidents and data from data sets to develop pattern matching algorithms or rules that define key variables for incidents. That is, a pattern or rule may be linked to an incident, via an incident identifier for example. Each incident identifier may be a unique serial number, token, and so on that identifies a particular type of incident. There may be multiple patterns linked to one incident via the same incident identifier if different sets of variables may suggest sufficient likelihood that the incident will occur. The occurrence of an incident may trigger the pattern matching module 24 to analyze monitored input data sets 14A, 14B, ... 14N related to the incident to identify key variables that also occurred at the time, date and location of the incident. Typically, pattern matching module 24 may require an incident to occur multiple times in order to identify the key variables that are common in the data sets 14A, 14B, ... 14N at each occurrence or a majority of occurrences of the incident. Pattern matching module 24 may correlate input data sets 14A, 14B, ... 14N based on incident type to identify variables or data elements common to each occurrence of the incident and link any generate patterns or rules to that incident.

Data sets 14A, 14B, ... 14N may include incident records and pattern matching module 24 may receive a notification that an incident occurred within a healthcare organization, such as a patient fall, and is operable to correlate that incident record to other data relating to conditions of the healthcare organization, based on the data elements date, time, and location for example. Pattern matching module 24 may be operable to determine that a specific door proximate to the location of the patient fall was left open and that it was raining on the date and at the time of the fall, or that the maintenance staff had just waxed the floors prior to the fall. Pattern matching module 24 may then identify the open door, its location, temperature, maintenance schedule as key variables for a pattern matching algorithm linked to predicting an incident of a patient fall.

In accordance with some embodiments, pattern matching module 24 may also be manually configured with pattern matching algorithms by receiving defined pattern matching algorithms or hints for key variables that may be linked to specific incidents from a user. For example, a user may input a specific data element (variable, parameter) to search for within the data sets, and pattern matching module 24 is operable to parse the data sets 14A, 14B, ... 14N for correlations between the specific data element and incidents. If a correlation is detected that it may be flagged for the user to configure a pattern for that incident to generate an alert. Pattern matching module 24 may also manually update pattern matching algorithms or rules that were automatically generated by the incident prediction system 10 to expand or contract the set of key variables defined by a given pattern matching algorithm.

Pattern matching module 24 is operable to analyze input data in (near) real time to identify whether the input data meets a rule or pattern and generate alerts if a pattern or rule is met. In some embodiments the analysis does not need to occur in real time to take advantage of low usage times of the healthcare organization's information technology systems.

Pattern matching module 24 is operable to perform the data mining or analysis on the data sets 14A, 14B, ... 14N by focusing on a subset of data relating only to a specific health care organization, or a specific incident type, date, location, time, or other data element of interest.

Pattern matching module 24 is operable to provide an enhanced surveillance system using pattern matching algorithms or rules particular to surveillance records. Pattern matching module 24 is operable to provide an enhanced infection prediction system using pattern matching algorithms particular to infection and disease records, the current status of particular patents, lab records, news records, and so on.

Incident prediction module 26 is operable to monitor input data and match the monitored input data sets 14A, 14B, ... 14N against the pattern matching algorithms to detect the occurrence of key variables or incidents associated with the pattern matching algorithms linked to specific incidents. If the incident prediction module 26 detects the occurrence of a particular pattern matching algorithm or rule (such as a pattern or set of key variables, another incident and so on) in the monitored input data sets 14A, 14B, ... 14N, then the incident prediction module 26 is operable to issue an healthcare incident prediction alert for the incident linked to that specific pattern matching algorithm. Incident prediction module 26 is operable to predict when an incident is likely to occur based on pattern matching algorithms generated automatically by training the incident prediction system 10 on historical data from data sets 14A, 14B, ... 14N associated with incidents.

In accordance with further embodiments, pattern matching module 24 may interact with weighting module 32 to assign a weight to specific variables defined by a pattern matching algorithm, so that a specific variable is accorded a higher or lower significance in a pattern or rule. The weight may be a static or fixed weight, or a relative weight that depends on other variables being present in the input data. The weight may change depending on received feedback or learning by the incident prediction system. For example, if a specific staff member is frequently involved in healthcare incidents relating to dosage errors then that specific variable (i.e. the staff member being on shift) will be assigned a higher weight for a pattern matching algorithm for healthcare incidents relating to dosage errors, such that when that staff member is on shift incident alerts relating to dosage errors may be generated more often, while also considering the presence of other factors of the rule or pattern, such as time of day and type of medication. For example, if a specific staff member is on the late shift then an alert may be generated and provided to a supervisor to warn them that an incident may occur relating to that staff member. However, for other staff members on the late shift an alert may not be generated. In such a case the key variable associated with the specific staff member may have a higher weight.

Pattern matching module 24 may also solicit feedback from user stations 18 while developing pattern matching algorithms to receive hints for investigation into correlations and to confirm that the pattern matching algorithm should be applied to monitored input data sets or when a pattern of data elements is detected in monitored input data, prior to storing the pattern matching algorithm in system 10.

Pattern matching module 24 may be operable to generate patterns or rules based on probabilities. For example, at the time or date an incident occurred a set of key variables may be present in a subset of data from the data sets 14A, 14B, . . . 14N specific to that date or time the incident occurred. Then pattern matching module 24 may check for other occurrences of that particular incident, use the date or time associated with the other occurrences of that particular incident to generate additional subset of data from the data sets 14A, 14B, . . . 14N specific to those dates or times. Pattern matching module 24 may then process each of those subsets of data to determine whether one or more those key variables are present. This may refine the set of initially identified key variables if in the majority of cases those variables are not present. Additional key variables may also be identified by correlating all subsets of data specific to the particular type of incident. Then when a refine set of key variables is determined for a particular type of incident, pattern matching module 24 may consider how often those set of key variables are present in the data when that type of incident does not occur to generate a probability of that incident occurring or not occurring when the set of key variables are present. If the probability is more than a predetermined percentage, such as 65%-80% for example, then those set of key variables may be used to generate a pattern or rule used to predict the occurrence of that particular type of incident.

Pattern matching module 24 is also operable to configure a pattern template to filter historical data from data sets 14A, 14B, . . . 14N through to identify key variables that are present. Accordingly, pattern matching module 24 may use a form of guided pattern detection. The pattern template may be generated based on business knowledge or known risk factors associated with incidents, that may be integrated into incident prediction system 10.

Pattern matching module 24 is also operable re-process data from data sets 14A, 14B, . . . 14N periodically over time to refine patterns and generate new patterns as the data set evolves, new incidents occur, new data sets are considered, and so on.

Pattern matching module 24 is also operable to refine rules and patterns based on feedback from users. For example, a rule may generate numerous alerts that are false-positives and a user may override, modify or delete that rule so that it no longer triggers alerts or add other key variables to the pattern, such as time of day, to limit when an alert is triggered by that rule.

Pattern matching module 24 is also operable to configure patterns and rules specific to particular incidents by identifying a concentration of data points in data relevant to the particular type of incident from data sets 14A, 14B, . . . 14N.

Pattern matching module 24 is further operable to identify a subset of data from the data sets 14A, 14B, . . . 14N that is relevant to a particular type of incident and generate a visualization of the data for provision to a user. The user may then identify potential risk factors or data elements that may be associated with the incident to provide a guide for further pattern detection by system.

As an example, pattern matching module 24 may be operable to generate a subset of data relating to falls on dates that had more than five falls. Then pattern matching module 24 may process this smaller subset of data to identify correlations associated with falls. Potential correlations may be provided to a user for validation. For example, more falls may occur at times when admission levels are high and staffing levels are low. This correlation may be used to build a rule or pattern for alerts. Further, visualizations of the subset of data and potential correlations may be used to generate visualizations for display to a user. The correlations may link a set of variables for use in generating a rule. The subset of data and potential correlations may be displayed to a user in different ways, and new data sets may be added to the subset for further processing to identify additional correlations.

Further, pattern matching module 24 is operable to receive data from standards organizations regarding potential risk factors and correlations related to incidents, and use this information to generate rules and patterns and detect correlations.

The input output devices 34 may be any device that allows for input, examples of which may include, but are not limited to, keyboards, microphones, speakers, a monitor or display screen that is used to electronically display data, printers, antenna, transceivers, camera, global positioning system, sensors, scanners and pointing devices. The memory store 38 include any type of computer readable memory that is located either internally or externally to the device 14 such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), or the like. The central processing unit 32 is used to execute programming instructions for operation of the incident prediction system 10 and may include any type of processor, such as, for example, any type of general-purpose microprocessor or microcontroller, a digital signal processing (DSP) processor, an application-specific integrated circuit (ASIC), a programmable read-only memory (PROM), or any combination thereof. The network interface 38 may be a wired and/or wireless network interface that allows the device to connect to the network 12.

Figure 3:
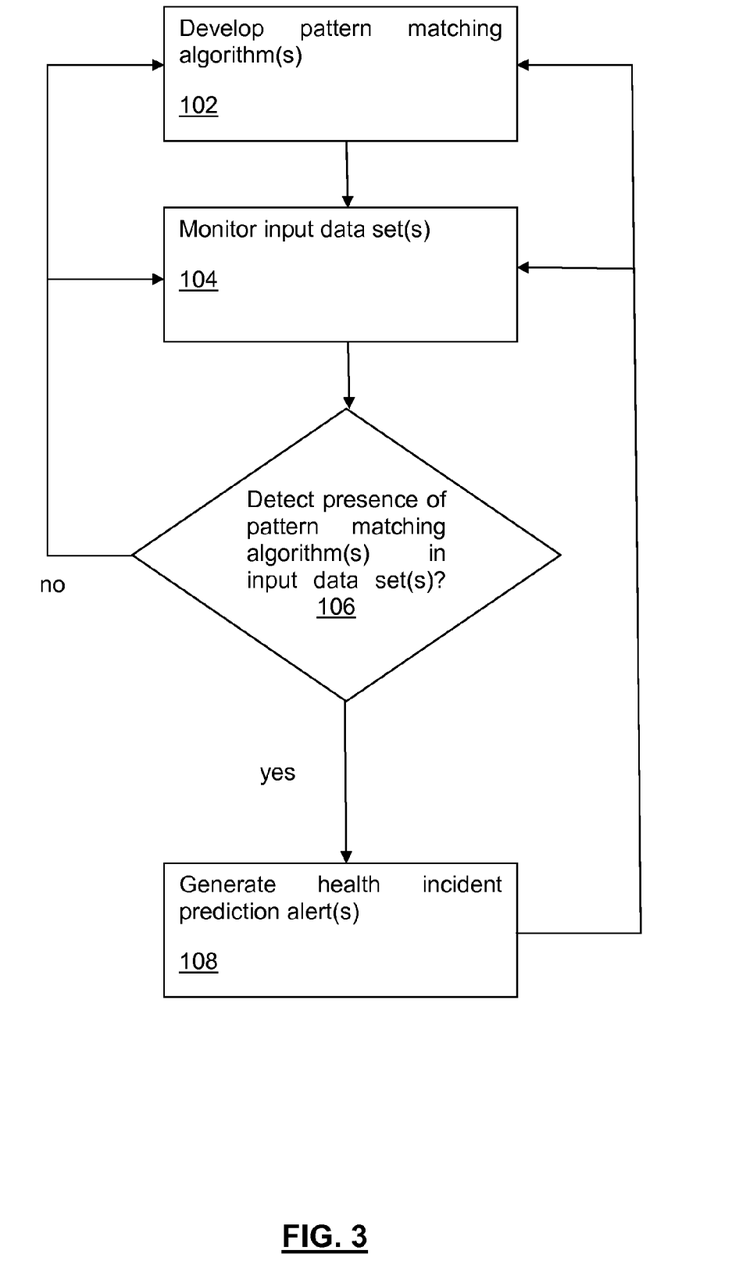
FIG. 3 is a flowchart diagram of a method for predicting health care incidents in accordance with at least one embodiment.

Reference is now made to FIG. 3, which illustrates a flowchart diagram of a method for predicting a healthcare incident implemented by incident prediction system 10 in accordance with at least one embodiment.

At step 102, incident prediction system 10 is operable to develop pattern matching algorithms using pattern matching module 24 and other components. A pattern matching algorithm defines a set of key variables linked to a healthcare incident, where the presence of the set of key variables in monitored input data suggests or predicts that a health care incident may occur. A pattern matching algorithm (pattern or rule) may also define an incident that suggests another incident may occur. A variable is a data element received by the incident prediction system 10 in data sets 14A, 14B, . . . 14N, where each variable (data element) may have an associated data value and data type. A variable may also identify an incident as a type and value. A data type for a variable may be a surgical device and the associated data value may be a device serial number. Patterns may be generated in a variety of ways, as described herein. For example, correlations present in data sets 14A, 14B, . . . 14N relevant to the incident may identify key variables that are present when the incident occurred. Pattern templates may be used for guided pattern matching based on known risk factors and business knowledge for example. Further, visualizations of subsets of data may be displayed and used to identify other variables or correlations. Pattern generation is an iterative process that may occur periodically to update and refine patterns over time. Correlations may be identified, rules or patterns of key variables may be constructed, those rules and patterns may be used to predict incidents, feedback may refine those rules, visualizations of data may be used to refine the rules or patterns, patterns may be shared and received from other health care organizations, and new incidents and data may further refine the patterns, rules and generate new ones.

Each pattern or rule is linked to one or more healthcare incidents, via an incident identifier for example. A particular incident may have one or more rules associated therewith Incident prediction system 10 matches monitored input data against the set of key variables defined by the pattern matching algorithm to predict that a healthcare incident linked thereto may occur. A pattern matching algorithm may be implemented as a rule in a rules engine, were each rule is defined by one or more conditions and one or more consequents. The condition may define the set of key variables (where is variable corresponds to a type and value) and the consequent may define the predicted incident.

The incident prediction system 10 is operable to automatically develop pattern matching algorithms by training or learning by mining data received in the form of data sets 14A, 14B, . . . 14N. For example, incident prediction system 10 may detect that an incident has repeatedly occurred and incident prediction system 10 may analyze the data sets 14 and a data repository 16 to determine whether there are one or more data elements are common to each incident occurrence (all present simultaneously when the incident occurs, or proximate to its occurrence), that may not be generally present at dates or times when the incident does not occur, thus suggesting correlation between the variables and the incident. Incident prediction system 10 may then automatically generate a pattern matching algorithm linked to that incident that defines as a variable set the one or more data elements that are common to each occurrence of the specific incident. In accordance with some embodiments, incident prediction system 10 may also consider whether the one or more data elements commonly occur when the incident does not occur, to develop a probability or likelihood of incident occurrence. For example, an incident may be providing the wrong dosage to a patient and this incident may repeatedly occur each time a particular staff member is working and the dosage is required to be administered at the end of that staff member's shift.

A pattern matching algorithm may be viewed as specific conditions that are often present when a given incident occurs such that the incident prediction system 10 can use a future simultaneous occurrence of those specific conditions to predict the incident reoccurring or to indicate that the incident has already occurred if not reported, and so on.

The incident prediction system 10 is operable to identify sets of commonly occurring data elements or variables in order to automatically generate pattern matching algorithms by correlating analyzed input data using date, time, and location, for example. For example, the incident prediction system 10 may consider input data related to a particular incident or location (such as a particular health care facility for example) to identify patterns of commonly occurring data elements.

Each pattern matching algorithm can define a narrow or wide set of variables for each incident. Further, one type of incident may be linked to multiple pattern matching algorithms. For example, if the incident is a patient fall then one pattern matching algorithm may define a threshold length of time since a healthcare provider last assisted a patient with going to the washroom, such as three hours for example, and that condition of a patient is impaired mobility. Another pattern matching algorithm linked to a patient fall may define the outside weather as raining and that a patient room is located proximate to an open outside door.

Key variables may be defined based on monitored input data set(s) 14A, 14B, . . . 14N. For example, by monitoring staffing records and shift records a key variable may be identified as the last day of a healthcare organization staff's shift, as the last day of shift may indicate that more mistakes will be made by that staff. A specific staff member may be a key variable if they are commonly involved in incidents. As another example, by monitoring inventory records a key variable may identified by the consumption record of a specific pill or a usage record for a specific device such as a pump. If the incident prediction system 10 detects that the same pump is involved in multiple incidents then it may be flagged as a key variable in a pattern matching algorithm as the pump may be erroneously calibrated, infected or otherwise not properly working. As a further example, government records may include product recall records which may be used as key variables to predict incidents associated with recalled products. As another example, maintenance records may indicate that a specific instrument has not been properly maintained and define that instrument as a key variable by type and value.

The incident prediction system 10 is also operable to be manually configured with pattern matching algorithms and is further operable to manually update automatically generated pattern matching algorithms. For example an administrator can manually define a pattern matching algorithm by specifying the key variables and the linked incident. In addition, the incident prediction system 10 can use feedback received from user stations 18A, 18B, for example, in order to further train, refine and update the pattern matching algorithms.

The incident prediction system 10 is operable to develop pattern matching algorithms during an initial period of time as well as continually develop pattern matching algorithms as new data is received and additional incident reports are received. The occurrence of an incident will trigger incident prediction system 10 to analyze input data sets (historic and current) for patterns of variables for use in defining the pattern matching algorithms.

The incident prediction system 10 is operable to assign weights to data elements to give a higher or lower weight to those data elements when developing a pattern matching algorithm. That is, incident prediction system 10 is operable to assign higher weights to important key variables to predict future events (incidents) based on past events. For example, patient specific data may be given more weight than other data elements when predicting incidents specific to that patient.

The incident prediction system 10 is further operable to query the user about a proposed pattern matching algorithm (i.e. asking if the incident actually did take place, albeit unreported, or is taking place).

A pattern matching pattern may also define an incident as predicting the occurrence of another incident. For example, an unexpected drug loss or theft may also indicate that a patient may overdose on the drug.

At step 104, incident prediction system 10 is operable to monitor input data, which may be received via input data module 22 from the data sets 14A, 14B, . . . 14N, the data repository 16, and so on. The incident prediction system 10 monitors input data to detect the presence of key variables that are associated with the pattern matching algorithms. In addition, incident prediction system 10 is operable to monitor input data to develop pattern matching algorithms by identifying patterns of variables that simultaneously occur at the same time as specific incidents.

At step 106, incident prediction system 10 is operable to apply one or more pattern matching algorithms (patterns or rules) to monitor near real time data sets 14A, 14B, . . . 14N to detect the presence of variables defined by one or more pattern matching algorithms in the monitored input data sets. A pattern matching algorithm defines a set of key variables and is linked to one or more incidents. A variable may be a data element that corresponds to a data value and data type. The incident prediction system 10 is operable to process the monitored input data using a variety of techniques in order to match the monitored input data against the pattern matching algorithms. That is, the incident prediction system 10 is operable to detect patterns of data elements in the monitored input data, where the patterns are associated with healthcare incidents.

If at step 106, incident prediction system 10 detects a set of key variables defined by one or more pattern matching algorithms in the input data sets, then incident prediction system 10 is operable to generate a healthcare incident prediction alert for each predicted incident linked to the one or more pattern matching algorithms. In accordance with some embodiments, the incident prediction alert may be transmitted to a user station 18 proximate to the location of the predicted incident so that a healthcare organization staff can act to prevent or alleviate the incident. Incident prediction system 10 is operable to receive feedback in relation to the alert to refine pattern matching algorithms. For example, a healthcare incident action alert may be ignored by the recipient and if the same alert is repeatedly ignored then the incident prediction system 10 may use this feedback to refine the pattern matching algorithm associated with the prediction alert. Incident prediction system 10 then returns to step 102 to continue developing pattern matching algorithms using the monitored input data, or to step 104 to continue monitoring the input data from the data sets 14A, 14B, . . . 14N or the data repository 60.

If at step 106, incident prediction system 10 does not detect key variables defined by one or more pattern matching algorithms in the input data sets 14A, 14B, . . . 14N or the data repository 60, then incident prediction system 10 returns to step 102 to continue developing pattern matching algorithms or to step 104 to continue monitoring the input data sets 14A, 14B, . . . 14N and data repository 60.

Embodiments have been described herein by way of example only. Various modification and variations may be made to these exemplary embodiments without departing from the spirit and scope of the invention, which is limited only by the appended claims.

The invention claimed is:

1. A computer implemented method for generating one or more incident prediction alerts for one or more health care organizations, the method comprising:
monitoring one or more data sets;
detecting an occurrence of a triggering event;
upon detecting the occurrence of the triggering event, developing one or more rules linked to the triggering event, wherein the triggering event comprises at least one incident that occurred or almost occurred at the one or more health care organizations; and
applying the one or more rules to the one or more data sets to detect the presence of one or more variables defined by the one or more rules;
wherein the one or more variables are linked to the conditions of the one or more health care organizations related to the at least one incident that occurred or almost occurred at the one or more health care organizations.

2. The method of claim 1 wherein the one or more data sets comprise one or more historical data sets relating to the at least one incident that occurred or almost occurred at the one or more health care organizations, and wherein developing the one or more rules comprise, for each incident that occurred or almost occurred at the one or more health care organizations, training on the one or more historical data sets to identify the one or more variables common to the at least one incident that occurred or almost occurred at the one or more health care organizations.

3. The method of claim 2 wherein the one or more data sets comprise one or more near-real time data feeds regarding machines, devices and patients of the one or more health care organizations and other data relevant to the one or more health care organizations for incident prediction.

4. The method of claim 3 further comprising normalizing the one or more near-real time data feeds, generating rules on the one or more historical data sets, generating the one or more incident prediction alerts by applying the one or more rules to the one or more near-real time data feeds, training to update the one or more rules, validating and error checking the one or more rules, removing statistical noise from the one or more near-real data feeds, generating visualizations for the one or more near-real data feeds, and receiving input and feedback data.

5. The method of claim 1 wherein the one or more rules are based on one or more pattern matching algorithms.

6. The method of claim 1 wherein each of the one or more variables comprise of a type and a value.

7. The method of claim 2 further comprising training on the one or more historical data sets to determine a probability of incident occurrence, and wherein at least one of the one or more incident prediction alerts is generated based on the probability of incident occurrence.

8. The method of claim 1, the method further comprising providing an interface for reporting occurrences of the at least one incident that occurred or almost occurred at the one or more health care organizations and receiving the one or more near-real data feeds relating to the occurrences of the at least one incident that occurred or almost occurred at the one or more health care organizations.

9. The method of claim 1, wherein the one or more incident prediction alerts comprise at least one of predictions, indications or other determinations that an incident has occurred or will likely occur.

10. A system comprising a processor and a non-transitory computer readable storage medium storing instructions which when executed by the processor, configure the processor to generate incident prediction alerts for one or more health care organizations by:

monitoring one or more data sets;

detecting an occurrence of a triggering event;

upon detecting the occurrence of the triggering event, developing one or more rules linked to the triggering event, wherein the triggering event comprises at least one incident that occurred almost occurred at the one or more health care organizations; and     applying the one or more rules to the one or more data sets to detect the presence of one or more variables defined by the one or more rules;

wherein the one or more variables are linked to the conditions of the one or more health care organizations related to the at least one incident that occurred or almost occurred at the one or more health care organizations.

11. The system of claim 10 wherein the one or more data sets comprise one or more historical data sets relating to the at least one incident that occurred or almost occurred at the one or more health care organizations, and wherein developing the one or more rules comprise for each incident that occurred or almost occurred at the one or more health care organizations, training on the one or more historical data sets to identify the one or more variables common to the at least one incident that occurred or almost occurred at the one or more health care organizations.

12. The system of claim 11 wherein the one or more data sets comprise one or more near-real time data feeds regarding machines, devices and patients of the one or more health care organizations and other data relevant to the one or more health care organizations for incident prediction.

13. The system of claim 12 wherein the processor is configured to normalize the one or more near-real time data feeds, generate rules on the one or more historical data sets, generate prediction alerts by applying the one or more rules to the one or more near-real time data feeds, train to update rules, validate and error check the one or more rules, remove statistical noise from the one or more near-real data feeds, generate visualizations for the one or more near-real data feeds, and receive input and feedback data.

14. The system of claim 10 wherein the processor is configured to develop the one or more rules based on one or more pattern matching algorithms.

15. The system of claim 10 wherein each of the one or more rules is linked to at least one of the one or more healthcare incidents, and each incident is linked to at least one of the one or more rules.

16. The system of claim 10 wherein each of the one or more variables comprise a type and a value.

17. The system of claim 11 wherein the processor is further configured to train on the one or more historical data sets to determine a probability of incident occurrence, and wherein at least one of the one or more incident prediction alerts is generated by the processor based on the probability of incident occurrence.

18. The system of claim 10 wherein the processor configured to provide an interface for reporting occurrences of the at least one incident that occurred or almost occurred at the one or more health care organizations and to receive the one or more near-real data feeds relating to the occurrences of the at least one incident that occurred or almost occurred at the one or more health care organizations.

19. The system of claim 10 wherein the one or more incident prediction alerts comprise at least one of predictions, indications or other determinations that an incident has occurred or will likely occur.

20. Non-transitory computer readable medium with instructions encoded thereon to configure a processor to generate one or more incident prediction alerts for transmission to one or more health care organization systems by:

monitoring one or more data sets;

detecting an occurrence of a triggering event;

upon detecting the occurrence of the triggering event, developing one or more rules linked to the triggering event, wherein the triggering event comprises at least one incident that occurred or almost occurred at the one or more health care organizations; and     applying the one or more rules to the one or more data sets to detect the presence of one or more variables defined by the one or more rules;

wherein the one or more variables are linked to the conditions of the one or more health care organizations related to the at least one incident that occurred or almost occurred at the one or more health care organizations.

21. The computer readable medium of claim 20 wherein the one or more data sets comprise one or more historical data sets relating to the at least one incident that occurred or almost occurred at the one or more health care organizations, and to further configure the processor to develop rules by, for each incident that occurred or almost occurred at the one or more health care organizations, training on the one or more historical data sets to identify the one or more variables common to the at least one incident at the one or more health care organization.

\* \* \* \* \*